(12) United States Patent
Foster et al.

(10) Patent No.: US 10,444,256 B2
(45) Date of Patent: Oct. 15, 2019

(54) DEVICE AND SYSTEM FOR RELATIVE MOTION SENSING

(71) Applicants: Ottis Charles Foster, McGregor, TX (US); Scott Miles Langerman, McGregor, TX (US); John Edward Fitch, Woodway, TX (US)

(72) Inventors: Ottis Charles Foster, McGregor, TX (US); Scott Miles Langerman, McGregor, TX (US); John Edward Fitch, Woodway, TX (US)

(73) Assignee: Structural Health Data Systems, Waco, TX (US)

( * ) Notice: Subject to any disclaimer, the term of this patent is extended or adjusted under 35 U.S.C. 154(b) by 456 days.

(21) Appl. No.: 14/821,354

(22) Filed: Aug. 7, 2015

(65) Prior Publication Data
US 2017/0038407 A1 Feb. 9, 2017

(51) Int. Cl.
*G01P 13/00* (2006.01)
*G01N 33/00* (2006.01)

(52) U.S. Cl.
CPC .......... *G01P 13/00* (2013.01); *G01N 33/0098* (2013.01)

(58) Field of Classification Search
None
See application file for complete search history.

(56) References Cited

U.S. PATENT DOCUMENTS

| | | | | |
|---|---|---|---|---|
| 3,010,063 A | * | 11/1961 | Rhoades | G05B 19/351 318/567 |
| 2011/0288789 A1 | * | 11/2011 | Henningson | G01R 19/16542 702/33 |
| 2013/0023290 A1 | * | 1/2013 | Rofougaran | G01S 7/412 455/456.3 |
| 2014/0312242 A1 | * | 10/2014 | Valentino | G01P 13/00 250/395 |
| 2015/0076929 A1 | * | 3/2015 | Elenga | H02K 41/0356 310/12.15 |
| 2015/0155732 A1 | * | 6/2015 | McCormick | H02J 7/0052 318/139 |
| 2015/0179332 A1 | * | 6/2015 | Ette | H01F 7/20 340/5.61 |

* cited by examiner

*Primary Examiner* — Alexander G Ghyka
(74) *Attorney, Agent, or Firm* — David G. Henry, Sr.

(57) ABSTRACT

The invention pertains to a device and system which uses printed circuit board metrology to accurately measure relative motion between surfaces in one or more dimensions. The invention comprises a system on a chip (SOC) to periodically measure, log, and transmit relative motion data in an automated fashion either wired or wirelessly, allowing long term measurement of moving surfaces such as foundation movement, bridge movement, concrete movement, structural system movement, excavation movement, slope monitoring or tree growth monitoring.

12 Claims, 6 Drawing Sheets

Relative Motion Sensor

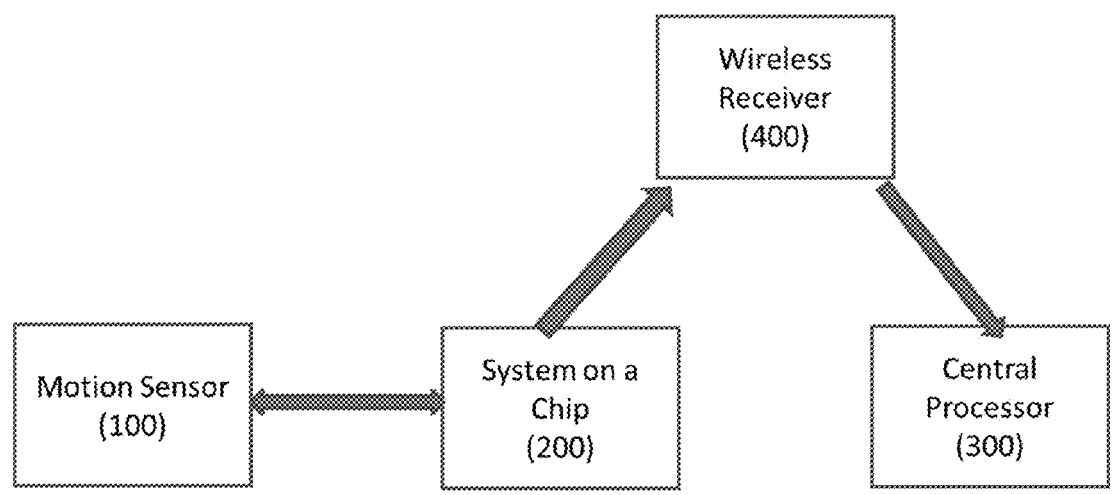
Figure 1 – System Components

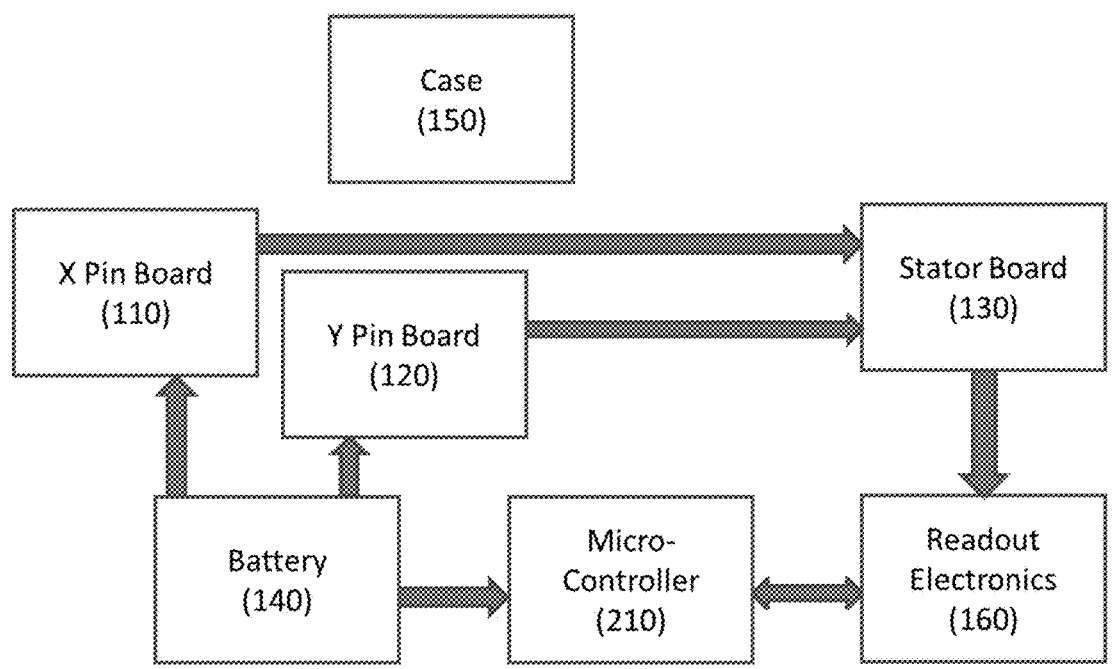
Figure 2 – Motion Sensor (100) Components

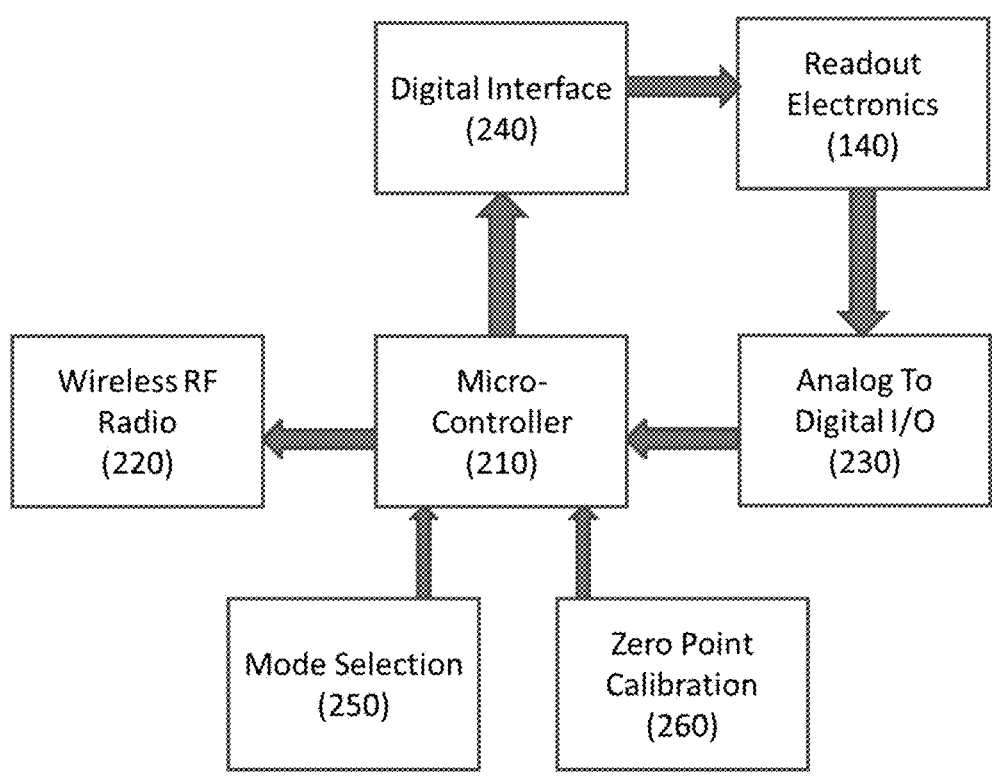
Figure 3 – SOC (200) Components

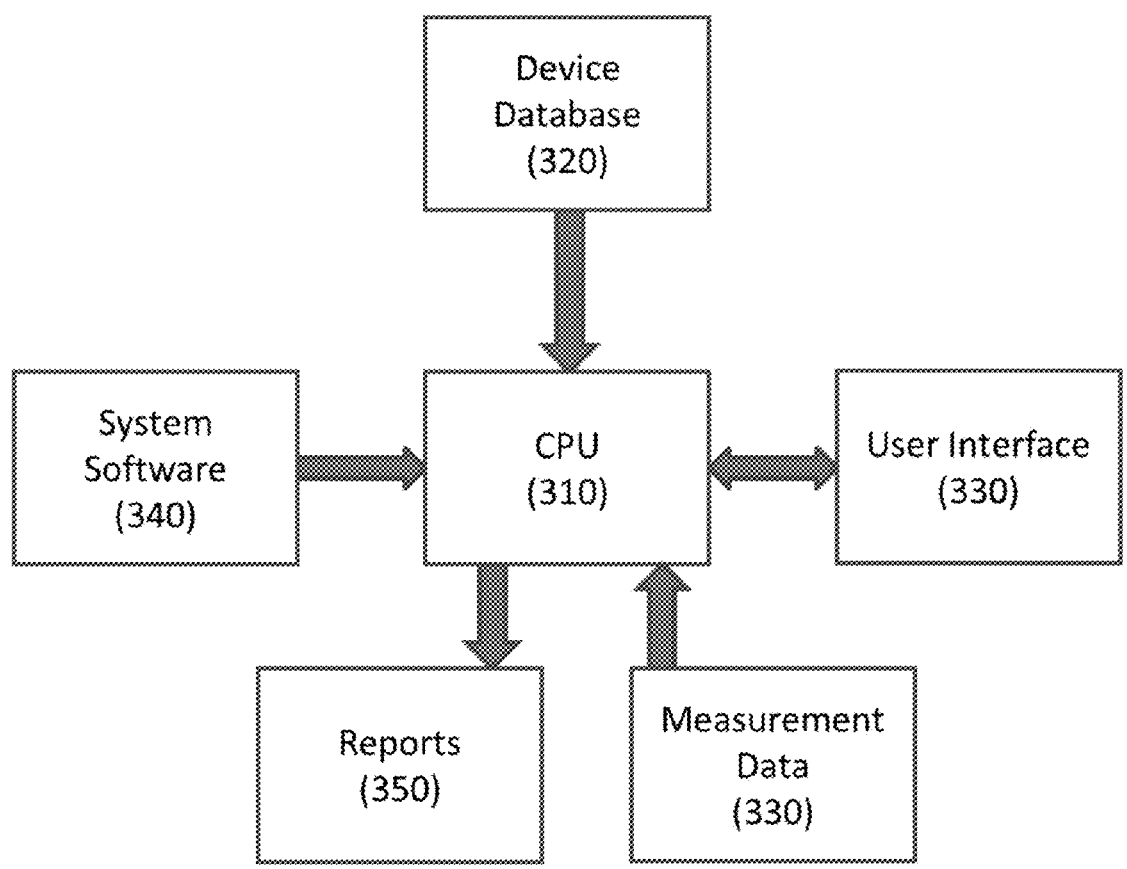
Figure 4 — Central Processor (300) Components

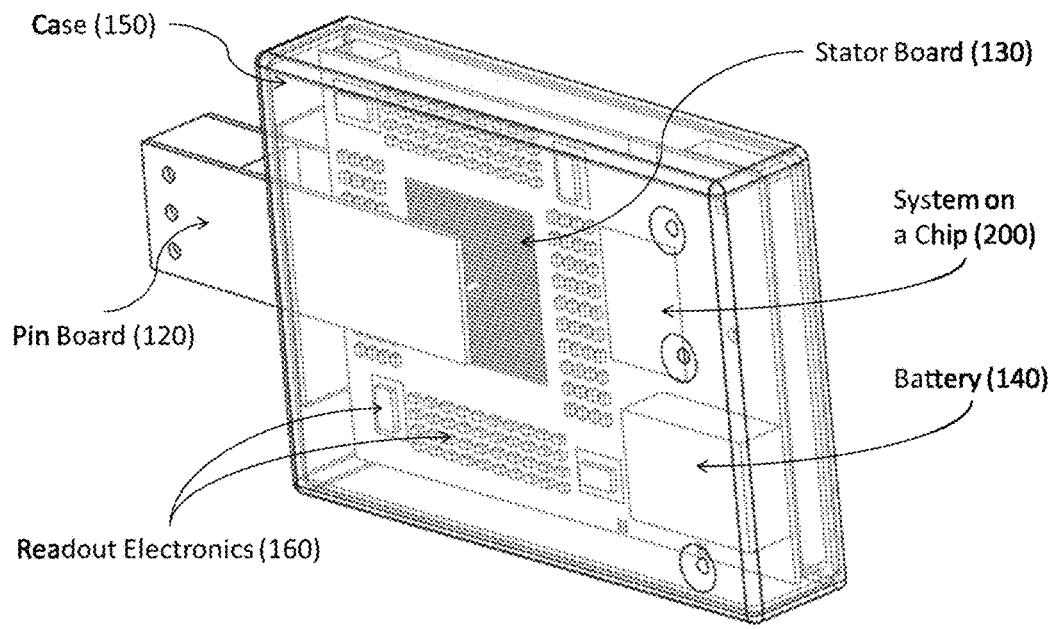
Figure 5 – Relative Motion Sensor
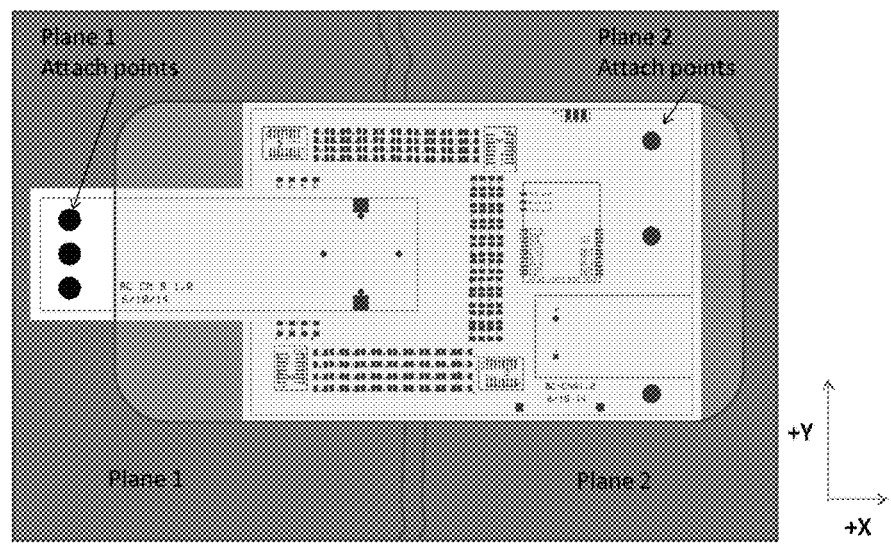
Figure 6 – Example install foundation monitoring

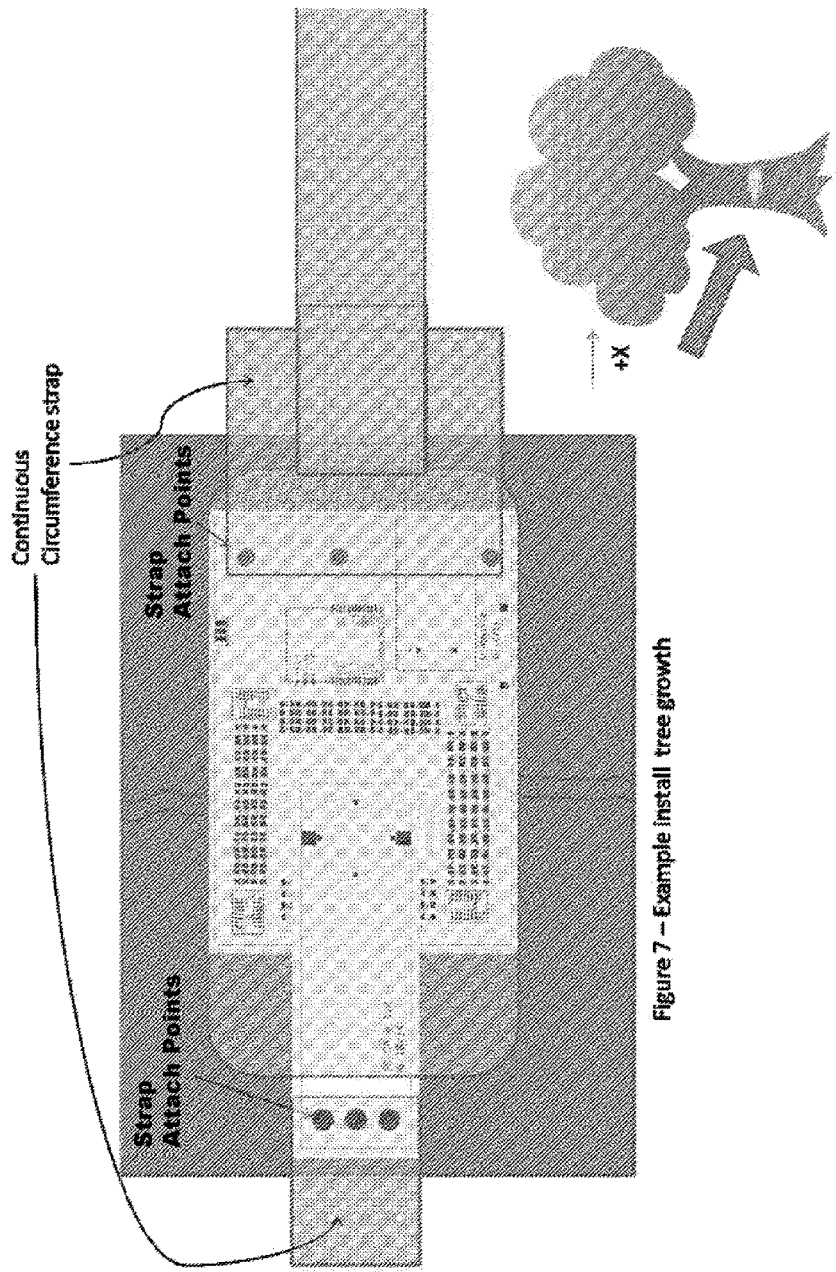

DEVICE AND SYSTEM FOR RELATIVE MOTION SENSING

BACKGROUND OF THE INVENTION

Long term, low cost, accurate monitoring of relative motion between objects, planes, or perimeter changes is required in a variety of industries. Typical measurements may span months or years and typically requires on site measurement on a periodic basis to establish accurate records and correlation for long term variations such as seasons, structural deflections, moisture content, etc. The device and method presented uses accurate metrology from PCB manufacturing processes, low power microcontroller and RF communications, and a simple readout schema to establish a unique device for long term relative motion sensing and data logging.

SUMMARY OF THE INVENTION

An object of the present invention is to provide a system for monitoring long term relative motions between surfaces or planes in one or more dimensions. Another object of the invention is to provide a device for accurately measuring and reporting the long term relative motions between surfaces or planes in one or more dimensions.

To achieve these objectives, the present invention comprises an electrical circuit that measures power on one or more parallel conductors, an electrical interface circuit that interprets the measured conductors, wired or wireless communications between a central control unit and individual devices, and a central control unit for data acquisition, data storage, data display, and data analysis algorithms.

DESCRIPTION OF THE DRAWINGS

FIG. 1 depicts an overall representation of the major system components comprising the motion sensing device (100), the System on a Chip (200), a wireless receiver for receipt of data from the system on a chip (400), and a central processor (400).

FIG. 2 represents the individual components comprising the Motion Sensor (100) including Pin Boards for various directions (110,120), a Stator Board (130), a battery or power source (140), readout electronics (160) and the case (150). FIG. 2 also shows the microcontroller (210) interaction with the motion sensor. In the current embodiment the microcontroller is one of the SOC components (200).

FIG. 3 represents the individual components comprising the system on a chip (200) including the microcontroller (210), Analog to digital interface (230), wireless RF radio (220), and digital interface (240). FIG. 3 also shows a mode selection input (250) and zero point calibration (260) as part of the current embodiment. FIG. 3 also shows the interaction with the readout electronics (140) as part of the motion sensor.

FIG. 4 represents the individual components comprising the central processor (300) including a CPU (310), User interface (330), System Software (340), Database of motion sensors (320), database of measurement data(330) and output reports (350).

FIG. 5 depicts an embodiment of the relative motion sensing device comprising the various components of the motion sensor (100) and system on a chip (200).

FIG. 6 depicts an embodiment of the relative motion device as might be installed for a foundation monitoring application. In this case the pin board(s) (110, 120) are installed on one plane and the stator board (130) is installed on a second plane allowing motion between the two planes. In this example, the measurement would be made in two orthogonal dimensions if two pin boards were installed.

FIG. 7 depicts an embodiment of the relative motion device as might be installed for a circumferential measurement such as a tree growth measurement. In this embodiment, a strap is attached around the item to be measured between the pin board and the stator board. As growth occurs the pin board moves in a single dimension on the stator board.

DETAILED DESCRIPTION

In the following description of the present invention there are multiple details established to provide a thorough understanding of the invention and the preferred implementations of the invention. It should be clear that the description is not intended to limit the invention to these specific embodiments and that variations, changes, substitutions, or equivalent components will be apparent to those skilled in the art and should not be considered significant differences from the intended scope of the invention.

The invention intends to measure relative motion and accurately report and log the information as a function of time. To accomplish this, the device utilizes the capability of printed circuit board manufacturing to establish precise metrology of parallel conductors on one or more sides of a printed circuit board (the stator board (130)). These parallel conductors are bare conductors allowing a connection from a second conductor (pin of the pin board (110,120) to apply a voltage from the battery to one or more of the parallel conductive lines on the stator board. In the current embodiment, the stator board has parallel conductors running in one direction on the top of the board and orthogonal parallel conductors running on the bottom of the board. Two pin boards and their associated pins span the stator board in such a way as to allow the pins to travel across conductors on the stator board as the stator and pin boards move relative to each other. The case (150) is designed to both protect the electronics and to physically ensure the pins are in contact with the parallel conductors through the full range of expected motion. In the current embodiment, the pins are micro spring connectors that allow motion in and out of the stator plane without loss of connection between the pins and the stator board.

In the current embodiment, the pin board may have multiple orthogonal pins as depicted in FIG. 6 and FIG. 7. With multiple orthogonal pins rotational information between the pin board and the stator board can also be determined using the metrology of the pin locations and the X and Y readouts of the multiple pins.

The readout electronics are established in such a way as to ensure that each parallel conductor is uniquely measured when queried by the SOC (200). This may be accomplished in several ways. One current embodiment uses a series of diodes and multiplexors to uniquely isolate each parallel conductor. The parallel conductors may be tied together in such a way as to physically encode the address in order to minimize the number of multiplexors required to readout the parallel conductors. If physical encoding is used, diodes isolate the encoded lines from each other. Encoding is accomplished in groups of parallel conductors that comprise a high order byte and a low order byte for the address of the parallel conductors.

Another embodiment uses direct measurement through individual resistors on each conductor to provide a voltage divider circuit that is read by the analog to digital convertor for unique conductor identification. If encoding is not used, then each individual conductor may be connected to an individual multiplexor input.

The SOC (200) uses a digital interface (240) (direct addressing, SPI, UART, or other control sequence), to query individual inputs directly or from the multiplexors. In the current embodiment, multiple multiplexors are grouped with the same control lines to minimize the digital interface requirements. The output of these grouped multiplexors are then input to an independently addressable multiplexor that allows the SOC to efficiently query each parallel conductor independently. The outputs of the second stage of multiplexors is input into the analog to digital interface (230) on the SOC. Any parallel conductor that is read as having a high voltage during the readout is stored in microcontroller memory until all parallel lines have been read out.

Because the physical size of the pin (110,120) may touch multiple parallel conductors at the same time, each position of the pin may cause one or more adjacent conductors to show as high. The algorithm in the microcontroller reviews all conductors showing as high and properly interpolates the physical position of the pin or pins on the stator board. This position is placed into a memory location for transmission via RF radio (220) or by wired interface for data log transfer.

In the current embodiment, the SOC includes the periodic wireless transfer of data to a wireless receiver (400) which transfers the data via wired or wireless interface to a central processor. In the current embodiment, the SOC accomplishes the readout of the electronics and transmission of the data approximately one time per hour. In between readouts, the SOC goes into low power sleep mode turning off all interfaces and powering down the readout electronics thereby providing years of power from a small battery. In the current embodiment, if no conductors on a given side show a pin position during a measurement, an error message is transmitted or logged.

In the current embodiment, two additional physical interrupts are identified to the SOC through physical buttons attached to the battery. The first interrupt allows a mode selection capability which may be used for various items. The current embodiment has a setup mode and a standard mode. In the setup mode, readouts and data logging and transmission are accomplished every 2 seconds for a number of minutes to allow verification of wireless or wired communications and ensure proper readout positioning. In standard mode the microcontroller goes into long periods of low power sleep mode (hours to days) between readings. In the current embodiment, the second interrupt establishes the zero point or start point of the measuring sequence. This is accomplished by setting up the device and when the interrupt is pushed, the initial readout is stored in SOC memory and is added to the data transmission for all future readouts to allow the central processor the ability to interpret the future readouts relative to the start point instead of as an absolute measurement relative to the parallel conductor position.

In the current embodiment, the Central Processor (300) consists of any computing platform with its inherent CPU, memory, and operating system. In the current embodiment, the device database and measurement data reside in either a flat file or a tabular SQL database. Measurement data from a device is stored along with it's associated timestamp. Software is provided to query devices and present the data in tabular or graphical form to the user. A series of standard reports are generated to present data in summary form to end users. The device database (320) also includes a series of user defined alarms or trigger points. In the event of an alarm limit being met, the cpu may automatically send information to the user interface such as an email notification. These limits include a low battery notification in the current embodiment.

In the current embodiment, several installation methods are anticipated for various applications. Individual mechanism for independently attaching the pin board to one side of the desired measurement and the stator board to the other side of a desired measurement are envisioned. Installation methods include mechanical attachments, adhesive attachments, and magnetic attachments. FIGS. 6 and 7 show two such configurations. It is not the intent of this invention to establish all of the applications and installation mechanisms for this system but to establish the unique aspects of the measurement device and overall system itself.

What is claimed is:

1. A motion sensing device comprising:
a printed circuit board (PCB) comprising a first plurality of parallel conductors and a second plurality of parallel conductors, said first plurality of parallel conductors being positioned on a first face of said printed circuit board, said second plurality of parallel conductors being positioned on an opposite face of said printed circuit board relative to said first face;
a power source coupled to said PCB; and
a first pin board comprising a first pin, said first pin board being configured for movement relative to said first face, said first pin being configured for electrical connectivity with at least one conductor of said first plurality of parallel conductors when said movement of said first pin is to a first juxtaposed position relative to said at least one conductor of said first plurality of parallel conductors and electrical discontinuity with one or more other conductors of said first plurality of parallel conductors.

2. The motion sensing device of claim 1 further comprising first attachment means for engaging said first pin board with a first surface area and second attachment means for engaging said PCB to a second surface area, whereby a change of spatial position of said first surface area relative to said second surface area produces said movement.

3. The motion sensing device of claim 2 wherein said first attachment means utilizes an adhesive.

4. The motion sensing device of claim 2 wherein said first attachment means utilizes a magnetic fixture.

5. The motion sensing device of claim 1 further comprising a voltage measuring means operably coupled to said at least one conductor of said first plurality of parallel conductors for measuring voltage of said at least one conductor of said first plurality of parallel conductors.

6. The motion sensing device of claim 5 wherein said voltage measuring means is a multiplexer.

7. The motion sensing device of claim 5 further comprising a digital interface means operably connected to said voltage measuring means for receiving data from said voltage measuring means and transmitting it to data storage means for storing said data.

8. The motion sensing device of claim 7 wherein said digital interface means is a system on a chip (SOC).

9. The motion sensing device of claim 7 wherein said data storage means is a remote computing platform comprising internal memory.

10. The motion sensing device of claim 1 wherein said first plurality of parallel conductors is physically encoded utilizing diodes to isolate groups of conductors of said first plurality of parallel conductors.

11. The motion sensing device of claim 1 wherein each conductor of said first plurality of parallel conductors is configured for direct measurement through individual resistors on said each conductor.

12. A motion sensing device comprising:
- a printed circuit board (PCB) comprising a first plurality of parallel conductors and a second plurality of parallel conductors, said first plurality of parallel conductors being positioned on a first face of said printed circuit board, said second plurality of parallel conductors being positioned on an opposite face of said printed circuit board relative to said first face;
- a power source coupled to said PCB; and
- a first pin board comprising a first pin, said first pin board being configured for movement relative to said first face, said first pin being configured for electrical connectivity with at least one conductor of said first plurality of parallel conductors when said movement of said first pin is to a first juxtaposed position relative to said at least one conductor of said first plurality of parallel conductors and electrical discontinuity with one or more other conductors of said first plurality of parallel conductors; and
- a second pin board comprising a second pin, said second pin board being configured for movement relative to said opposite face, said second pin being configured for electrical connectivity with at least one conductor of said second plurality of parallel conductors when said movement of said second pin is to a first juxtaposed position relative to said at least one conductor of said second plurality of parallel conductors and electrical discontinuity with one or more other conductors of said second plurality of parallel conductors.

\* \* \* \* \*